(12) United States Patent
Bos et al.

(10) Patent No.: US 10,017,432 B2
(45) Date of Patent: *Jul. 10, 2018

(54) ALKANE OXIDATIVE DEHYDROGENATION AND/OR ALKENE OXIDATION

(71) Applicant: SHELL OIL COMPANY, Houston, TX (US)

(72) Inventors: Alouisius Nicolaas Renée Bos, Amsterdam (NL); Ronald Jan Schoonebeek, Amsterdam (NL); Frank Spies, Amsterdam (NL); Michiel Johannes Franciscus Maria Verhaak, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/101,012

(22) PCT Filed: Dec. 4, 2014

(86) PCT No.: PCT/EP2014/076551
§ 371 (c)(1),
(2) Date: Jun. 2, 2016

(87) PCT Pub. No.: WO2015/082602
PCT Pub. Date: Jun. 11, 2015

(65) Prior Publication Data
US 2016/0304414 A1    Oct. 20, 2016

(30) Foreign Application Priority Data

Dec. 6, 2013  (EP) .................................... 13196065

(51) Int. Cl.
| | | |
|---|---|---|
| C07C 51/16 | (2006.01) | |
| C07C 5/48 | (2006.01) | |
| C07C 51/25 | (2006.01) | |
| B01J 37/03 | (2006.01) | |
| B01J 27/057 | (2006.01) | |
| B01J 35/02 | (2006.01) | |
| B01J 37/00 | (2006.01) | |

(52) U.S. Cl.
CPC ............. *C07C 5/48* (2013.01); *B01J 27/0576* (2013.01); *B01J 35/023* (2013.01); *B01J 37/0036* (2013.01); *B01J 37/031* (2013.01); *C07C 51/25* (2013.01); *C07C 51/252* (2013.01); *B01J 2523/00* (2013.01); *C07C 2523/20* (2013.01); *C07C 2523/22* (2013.01); *C07C 2523/28* (2013.01); *C07C 2527/057* (2013.01); *Y02P 20/52* (2015.11)

(58) Field of Classification Search
None
See application file for complete search history.

(56) References Cited

U.S. PATENT DOCUMENTS

| | | | | |
|---|---|---|---|---|
| 3,801,634 | A * | 4/1974 | Krabetz et al. ............ | B01J 8/06 562/532 |
| 6,130,183 | A * | 10/2000 | Herskowitz ............ | B01J 23/007 502/224 |
| 7,019,168 | B2 | 3/2006 | Dieterle et al. | |
| 7,091,377 | B2 | 8/2006 | Borgmeier et al. | |
| 8,242,048 | B2 * | 8/2012 | Rosen ...................... | B01J 21/04 502/312 |
| 2004/0147393 | A1 | 7/2004 | Hibst et al. | |
| 2010/0256432 | A1 | 7/2010 | Arnold et al. | |
| 2013/0072737 | A1 | 3/2013 | Kustov et al. | |

FOREIGN PATENT DOCUMENTS

| | | |
|---|---|---|
| EP | 261264 | 3/1988 |
| WO | 2003064035 | 8/2003 |
| WO | 2010096909 | 9/2010 |
| WO | 2013/164418 | † 11/2013 |
| WO | WO 2013164418 A1 * | 11/2013 ............ B01J 37/031 |

OTHER PUBLICATIONS

Harriott, "Chemical Reactor Design", Marcel Dekker, Inc., 2003, pp. 89-92.*
International Search Report of PCT/EP2014/076551 filed Dec. 4, 2014.
Harriott, "Chemical Reactor Design", Marcel Dekker, Inc., (2003), pp. 89-92.†

\* cited by examiner
† cited by third party

*Primary Examiner* — Sudhakar Katakam
*Assistant Examiner* — Ana Z Muresan

(57) ABSTRACT

The invention relates to a process of the oxidative dehydrogenation of an alkane containing 2 to 6 carbon atoms and/or the oxidation of an alkene containing 2 to 6 carbon atoms, wherein a gas stream comprising oxygen and the alkane and/or alkene is contacted with a mixed metal oxide catalyst containing molybdenum, vanadium, niobium and optionally tellurium, and wherein the weight hourly space velocity is of from 2.1 to 25.0 $hr^{-1}$ and the temperature is of from 300 to 500° C.

6 Claims, 1 Drawing Sheet

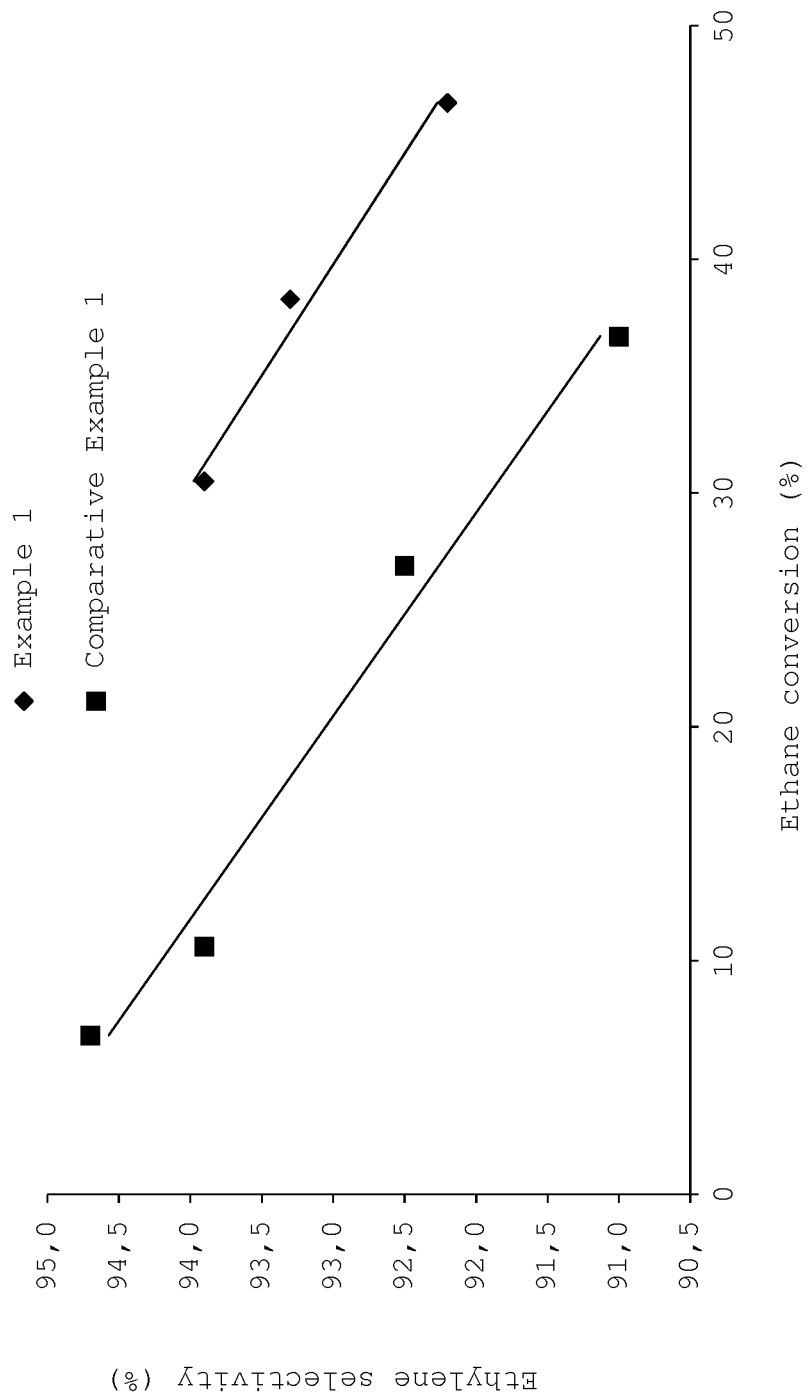

ALKANE OXIDATIVE DEHYDROGENATION
AND/OR ALKENE OXIDATION

PRIORITY CLAIM

The present application is the National Stage (§ 371) of International Application No. PCT/EP2014/076551 filed Dec. 4, 2014, which claims priority from European Patent Application No 13196065.0, filed Dec. 6, 2013 incorporated herein by reference.

FIELD OF THE INVENTION

The present invention relates to a process of alkane oxidative dehydrogenation (oxydehydrogenation; ODH) and/or alkene oxidation.

BACKGROUND OF THE INVENTION

It is known to oxidatively dehydrogenate alkanes, such as alkanes containing 2 to 6 carbon atoms, for example ethane or propane resulting in ethylene and propylene, respectively, in an oxidative dehydrogenation (oxydehydrogenation; ODH) process. Examples of alkane ODH processes, including catalysts and other process conditions, are for example disclosed in U.S. Pat. No. 7,091,377, WO2003064035, US20040147393, WO2010096909 and US20100256432. Mixed metal oxide catalysts containing molybdenum (Mo), vanadium (V), niobium (Nb) and optionally tellurium (Te) as the metals, can be used as such oxydehydrogenation catalysts. Such catalysts may also be used in the direct oxidation of alkenes to carboxylic acids, such as in the oxidation of alkenes containing 2 to 6 carbon atoms, for example ethylene or propylene resulting in acetic acid and acrylic acid, respectively.

It is an objective of the present invention to provide an alkane ODH and/or alkene oxidation process, wherein a mixed metal oxide catalyst containing Mo, V, Nb and optionally Te is used, which process is performed such that a relatively high activity and/or a relatively high selectivity is or are obtained.

SUMMARY OF THE INVENTION

Surprisingly it was found that one or more of the above-mentioned objectives can be obtained by means of an alkane ODH and/or alkene oxidation process, wherein the weight hourly space velocity is of from 2.1 to 25.0 hr$^{-1}$ and the temperature is of from 300 to 500° C.

Accordingly, the present invention relates to a process of the oxidative dehydrogenation of an alkane containing 2 to 6 carbon atoms and/or the oxidation of an alkene containing 2 to 6 carbon atoms, wherein a gas stream comprising oxygen and the alkane and/or alkene is contacted with a mixed metal oxide catalyst containing molybdenum, vanadium, niobium and optionally tellurium, and wherein the weight hourly space velocity is of from 2.1 to 25.0 hr$^{-1}$ and the temperature is of from 300 to 500° C.

BRIEF DESCRIPTION OF THE DRAWINGS

FIG. 1 shows a graph wherein for experiments from Example 1 and Comparative Example 1, wherein ethane ODH was performed, data for the conversion of ethane and the selectivity towards ethylene are included.

DETAILED DESCRIPTION OF THE INVENTION

In the present invention, the weight hourly space velocity is of from 2.1 to 25.0 hr$^{-1}$ and the temperature is of from 300 to 500° C., in a process wherein a gas stream comprising oxygen and the alkane and/or alkene through a reactor is contacted with a mixed metal oxide catalyst containing molybdenum, vanadium, niobium and optionally tellurium inside that reactor. It has surprisingly been found that when both the weight hourly space velocity and the temperature are relatively high, as described hereinbefore, higher selectivities are obtained at the same conversion or, conversely, higher conversions are obtained at the same selectivity.

Preferably, in the present invention, the mixed metal oxide catalyst containing molybdenum, vanadium, niobium and optionally tellurium is a heterogeneous catalyst in the form of particles, in other words a particulate catalyst. Preferably, said particulate catalyst (catalyst particles) is porous. Porous particles contain pores. This means that pores are present inside the porous particles. Inside the reactor, these heterogeneous catalyst particles make up a catalyst bed through which the gas stream comprising oxygen and the alkane and/or alkene is sent. In addition to catalyst particles, the catalyst bed may also contain inert (that is to say, catalytically inactive) particles.

In the alkane oxidative dehydrogenation process and/or alkene oxidation process of the present invention, the weight hourly space velocity (WHSV; in kg gas/kg catalyst/hr) is of from 2.1 to 25.0 hr$^{-1}$, preferably of from 4.0 to 18.0 hr$^{-1}$, more preferably of from 6.0 to 13.0 hr$^{-1}$, most preferably of from 7.0 to 11.0 hr$^{-1}$.

Preferably, said WHSV is at least 2.5 hr$^{-1}$, more preferably at least 3.0 hr$^{-1}$, more preferably at least 3.5 hr$^{-1}$, more preferably at least 4.0 hr$^{-1}$, more preferably at least 4.5 hr$^{-1}$, more preferably at least 5.0 hr$^{-1}$, more preferably at least 5.5 hr$^{-1}$, more preferably at least 6.0 hr$^{-1}$, more preferably at least 6.5 hr$^{-1}$, more preferably at least 7.0 hr$^{-1}$, more preferably at least 7.5 hr$^{-1}$, most preferably at least 8.0 hr$^{-1}$.

Further, preferably, said WHSV is at most 22.0 hr$^{-1}$, more preferably at most 20.0 hr$^{-1}$, more preferably at most 18.0 hr$^{-1}$, more preferably at most 16.0 hr$^{-1}$, more preferably at most 15.0 hr$^{-1}$, more preferably at most 14.0 hr$^{-1}$, more preferably at most 13.0 hr$^{-1}$, more preferably at most 12.5 hr$^{-1}$, most preferably at most 12.0 hr$^{-1}$, more preferably at most 11.5 hr$^{-1}$, more preferably at most 11.0 hr$^{-1}$, more preferably at most 10.5 hr$^{-1}$, most preferably at most 10.0 hr$^{-1}$.

Said "weight hourly space velocity" (WHSV) is defined by the following quotient: the entering hourly weight flow rate of the reactants/the catalyst bed weight. Thus, said WHSV indicates how many catalyst bed weights of feed can be treated per hour in a certain catalyst bed. In the present invention, said WHSV is therefore the quotient of the hourly weight flow rate (in kg/hr) of the gas stream comprising oxygen and the alkane and/or alkene, which gas stream in the present invention is contacted with the mixed metal oxide catalyst, divided by the catalyst bed weight (in kg). In determining said WHSV, the weight of any inert particles present in the catalyst bed is not taken into account. This means that the above-mentioned "catalyst bed weight", needed for calculating said WHSV, does not include the weight of any inert particles present in the catalyst bed. Further, in the present specification, said "catalyst bed weight" does not include the weight of any binder present in the catalyst particles. Such binder may for example be used in order to get a high strength catalyst for use in a fixed-bed application. If the weight of binder in the catalyst particles is known, the WHSV may be calculated in accordance with the present specification wherein the weight of such binder is not taken into account, as described hereinabove. The foregoing implies that in relation to determining said WHSV, the above-mentioned "catalyst bed weight" in the present specification consists of the weight of the catalytically active material, that is to say not including the weight of any inert material, such as binder.

Further, in the alkane oxidative dehydrogenation process and/or alkene oxidation process of the present invention, the temperature is of from 300 to 500° C., preferably of from 310 to 450° C., more preferably of from 320 to 420° C., most preferably of from 330 to 420° C.

Preferably, said temperature is at least 310° C., more preferably at least 320° C., more preferably at least 330° C., more preferably at least 340° C., more preferably at least 345° C., more preferably at least 350° C., more preferably at least 355° C., most preferably at least 360° C.

Further, preferably, said temperature is at most 480° C., more preferably at most 460° C., more preferably at most 450° C., more preferably at most 440° C., more preferably at most 430° C., more preferably at most 420° C., more preferably at most 410° C., most preferably at most 400° C.

Still further, in the alkane oxidative dehydrogenation process and/or alkene oxidation process of the present invention, typical pressures are 0.1-20 bara (i.e. "bar absolute"). Further, in a preferred embodiment of the present invention, the pressure is of from 0.1 to 15 bara, more preferably of from 0.5 to 10 bara, most preferably of from 1 to 5 bara.

In the present invention, one gas stream comprising oxygen and the alkane and/or alkene may be fed to the reactor. Alternatively, two or more gas streams may be fed to the reactor, which gas streams form a combined gas stream inside the reactor. For example, one gas stream comprising oxygen and another gas stream comprising an alkane, such as ethane, may be fed to the reactor separately. Said one gas stream or multiple gas streams may additionally comprise an inert gas, as further described below.

Preferably, in the alkane oxidative dehydrogenation process of the present invention, the alkane containing 2 to 6 carbon atoms is a linear alkane in which case said alkane may be selected from the group consisting of ethane, propane, butane, pentane and hexane. Further, preferably, said alkane contains 2 to 4 carbon atoms and is selected from the group consisting of ethane, propane and butane. More preferably, said alkane is ethane or propane. Most preferably, said alkane is ethane.

Further, preferably, in the alkene oxidation process of the present invention, the alkene containing 2 to 6 carbon atoms is a linear alkene in which case said alkene may be selected from the group consisting of ethylene, propylene, butene, pentene and hexene. Further, preferably, said alkene contains 2 to 4 carbon atoms and is selected from the group consisting of ethylene, propylene and butene. More preferably, said alkene is ethylene or propylene.

The product of said alkane oxidative dehydrogenation process may comprise the dehydrogenated equivalent of the alkane, that is to say the corresponding alkene. For example, in the case of ethane such product may comprise ethylene, in the case of propane such product may comprise propylene, and so on. Such dehydrogenated equivalent of the alkane is initially formed in said alkane oxidative dehydrogenation process. However, in said same process, said dehydrogenated equivalent may be further oxidized under the same conditions into the corresponding carboxylic acid which may or may not contain one or more unsaturated double carbon-carbon bonds. As mentioned above, it is preferred that the alkane containing 2 to 6 carbon atoms is ethane or propane. In the case of ethane, the product of said alkane oxidative dehydrogenation process may comprise ethylene and/or acetic acid, preferably ethylene. Further, in the case of propane, the product of said alkane oxidative dehydrogenation process may comprise propylene and/or acrylic acid, preferably acrylic acid.

The product of said alkene oxidation process comprises the oxidized equivalent of the alkene. Preferably, said oxidized equivalent of the alkene is the corresponding carboxylic acid. Said carboxylic acid may or may not contain one or more unsaturated double carbon-carbon bonds. As mentioned above, it is preferred that the alkene containing 2 to 6 carbon atoms is ethylene or propylene. In the case of ethylene, the product of said alkene oxidation process may comprise acetic acid. Further, in the case of propylene, the product of said alkene oxidation process may comprise acrylic acid.

The present alkane oxidative dehydrogenation process and/or alkene oxidation process comprises contacting a gas stream comprising oxygen ($O_2$) and the alkane and/or alkene with the mixed metal oxide catalyst. Said gas stream may be a combination of 2 gas streams being fed separately to the reactor, one gas stream comprising the oxygen and one gas stream comprising the alkane and/or alkene. Additionally, said gas stream comprising oxygen and the alkane and/or alkene may contain an inert gas. Said inert gas may be selected from the group consisting of the noble gases and nitrogen ($N_2$). Preferably, the inert gas is nitrogen or argon, more preferably nitrogen. Said oxygen ($O_2$) is an oxidizing agent, thereby resulting in oxidative dehydrogenation of the alkane and/or oxidation of the alkene. Said oxygen may originate from any source, such as for example air.

Ranges for the molar ratio of oxygen to the alkane and/or alkene in said gas stream which are suitable, are of from 0.01 to 1, more suitably 0.05 to 0.5. Furthermore, in a preferred embodiment, said gas stream comprises 5 to 35 vol. % of oxygen, more suitably 15 to 25 vol. % of oxygen, and 40 to 80 vol. % of the alkane and/or alkene, more suitably 50 to 70 vol. % of the alkane and/or alkene, and less than 80 (0 to 80) vol. % of the above-mentioned inert gas, more suitably less than 50 (0 to 50) vol. % of said inert gas, more suitably 5 to 35 vol. % of said inert gas, most suitably 10 to 20 vol. % of said inert gas. In the context of the present invention, the components of said gas stream are to be selected in an overall amount not to exceed 100 vol. %.

Said ratio of oxygen to the alkane and/or alkene and said volume percentages for oxygen, the alkane and/or alkene and said inert gas are the ratio and volume percentages, respectively, at the entrance of the catalyst bed. Obviously, after entering the catalyst bed, at least part of the oxygen and alkane and/or alkene from the gas stream gets consumed.

In the present invention, the catalyst is a mixed metal oxide catalyst containing molybdenum, vanadium, niobium and optionally tellurium as the metals, which catalyst may have the following formula:

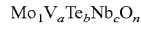

wherein:

a, b, c and n represent the ratio of the molar amount of the element in question to the molar amount of molybdenum (Mo);

a (for V) is from 0.01 to 1, preferably 0.05 to 0.60, more preferably 0.10 to 0.40, more preferably 0.20 to 0.35, most preferably 0.25 to 0.30;

b (for Te) is 0 or from >0 to 1, preferably 0.01 to 0.40, more preferably 0.05 to 0.30, more preferably 0.05 to 0.20, most preferably 0.09 to 0.15;

c (for Nb) is from >0 to 1, preferably 0.01 to 0.40, more preferably 0.05 to 0.30, more preferably 0.10 to 0.25, most preferably 0.14 to 0.20; and n (for O) is a number which is determined by the valency and frequency of elements other than oxygen.

Examples of oxydehydrogenation processes, including catalysts and other process conditions, are for example disclosed in above-mentioned U.S. Pat. No. 7,091,377, WO2003064035, US20040147393, WO2010096909 and US20100256432, the disclosures of which are herein incorporated by reference.

The amount of the catalyst in said process is not essential. Preferably, a catalytically effective amount of the catalyst is used, that is to say an amount sufficient to promote the alkane oxydehydrogenation and/or alkene oxidation reaction.

In general, the product stream comprises water in addition to the desired product. Water may easily be separated from said product stream, for example by cooling down the product stream from the reaction temperature to a lower temperature, for example room temperature, so that the water condenses and can then be separated from the product stream.

The invention is further illustrated by the following Examples.

EXAMPLES

(A) Preparation of the Catalyst

A mixed metal oxide catalyst containing molybdenum (Mo), vanadium (V), niobium (Nb) and tellurium (Te) was prepared, for which catalyst the molar ratio of said 4 metals was $Mo_1V_{0.29}Nb_{0.17}Te_{0.12}$.

Two solutions were prepared. Solution 1 was obtained by dissolving 15.8 g of ammonium niobate oxalate and 4.0 g of anhydrous oxalic acid in 160 ml of water at room temperature. Solution 2 was prepared by dissolving 35.6 g of ammonium heptamolybdate, 6.9 g of ammonium metavanadate and 5.8 g of telluric acid ($Te(OH)_6$) in 200 ml of water at 70° C. 7.0 g of concentrated nitric acid was then added to solution 2. The 2 solutions were combined which yielded an orange gel-like precipitate. The mixture was evaporated to dryness with the aid of a rotating evaporator ("rotavap") at 50° C.

The dried material was further dried in static air at 120° C. for 16 hours, milled to a fine powder and then calcined in static air at a temperature of 300° C. for 5 hours. After the air calcination, the material was further calcined in a nitrogen ($N_2$) stream at 600° C. for 2 hours. Then the material was treated with an aqueous 5% oxalic acid solution at 80° C. and filtered and dried at 120° C.

The dried catalyst powder was pressed into pills which pills were then milled. The milled material was then sieved using a sieve having a mesh size of 40-80 mesh. The sieved material, having a size of 40-80 mesh and composed of porous catalyst particles, was then used in the ethane oxidative dehydrogenation experiments described below. No binder was used in the preparation of said catalyst. The catalyst thus prepared is the "catalytically active material" as referred to above in the definition of "catalyst bed weight" which catalyst bed weight is used to determine the weight hourly space velocity (WHSV).

(B) Catalytic Oxidative Dehydrogenation of Ethane

Example 1: High Temperature and High WHSV

In Example 1, the catalyst thus prepared was used in a number of experiments involving ethane oxidative dehydrogenation within a small-scale testing unit comprising a vertically oriented, cylindrical, quartz reactor having an inner diameter of 4.6 mm. 4.04 g of the catalyst were loaded in the reactor. The catalyst bed height was 31 cm. In addition to the catalyst particles, the catalyst bed also contained inert silicium carbide (SiC) particles having an average diameter of 0.8 mm, wherein the volume ratio of catalyst particles to inert particles was 1:1.

In these experiments, a gas stream comprising 64 vol. % of ethane, 21 vol. % of oxygen ($O_2$) and 15 vol. % of nitrogen ($N_2$) was fed to the top of the reactor and then sent downwardly through the catalyst bed to the bottom of the reactor. Said gas stream was a combined gas stream comprising a flow of ethane having a rate of 17.01 Nl/hr, a flow of oxygen having a rate of 5.67 Nl/hr and a flow of nitrogen having a rate of 4.05 Nl/hr. "Nl" stands for "normal liter" as measured at standard temperature and pressure, namely 32° F. (0° C.) and 1 bara (100 kPa). Further, the weight hourly space velocity (WHSV) was 8.9 kg/kg catalyst/hr. The pressure in the reactor was 2.3 bara.

The temperature in the reactor for each of the experiments in Example 1 is shown in Table 1 below.

The conversion of ethane and the product composition were measured with a gas chromatograph (GC) equipped with a thermal conductivity detector (TCD) and with another GC equipped with a flame ionization detector. The water from the reaction was trapped in a quench pot.

In Table 1 below, the experimental results (conversion of ethane and selectivity towards ethylene) for Example 1 are shown.

TABLE 1

| Exp. | Temperature (° C.) | Conversion of ethane (%) | Selectivity to ethylene (%) |
|---|---|---|---|
| 1 | 366 | 30.5 | 93.9 |
| 2 | 376 | 38.3 | 93.3 |
| 3 | 386 | 46.7 | 92.2 |

Comparative Example 1: Low Temperature and Low WHSV

In Comparative Example 1, the procedure of Example 1 was repeated with the following differences:

1. 9.8 g of the catalyst were used.
2. The catalyst bed did not contain inert silicium carbide (SiC) particles.
3. The catalyst bed height was 38.5 cm.
4. The combined gas stream comprised a flow of ethane having a rate of 9.45 Nl/hr, a flow of oxygen having a rate of 3.15 Nl/hr and a flow of nitrogen having a rate of 2.25 Nl/hr. The volume percentages of ethane, oxygen and nitrogen were the same.
5. The WHSV was lower, namely 2.0 kg/kg catalyst/hr.
6. The temperature was lower.

The temperature in the reactor for each of the experiments in Comparative Example 1 is shown in Table 2 below.

Further, in said table, the experimental results (conversion of ethane and selectivity towards ethylene) for Comparative Example 1 are shown.

TABLE 2

| Exp. | Temperature (° C.) | Conversion of ethane (%) | Selectivity to ethylene (%) |
|---|---|---|---|
| 1 | 281 | 6.8 | 94.7 |
| 2 | 291 | 10.6 | 93.9 |
| 3 | 319 | 26.9 | 92.5 |
| 4 | 329 | 36.7 | 91 |

In FIG. 1, a graph is shown wherein for each of the experiments from Example 1 and Comparative Example 1 (see Tables 1 and 2 above), data for the conversion of ethane (on the x-axis) and the selectivity towards ethylene (on the y-axis) are shown. Further, in FIG. 1, for each of Example 1 and Comparative Example 1, a straight "best fit" line is drawn connecting these conversion/selectivity data points.

Surprisingly, it appears from FIG. 1 that for the experiments of the present invention (Example 1) wherein a relatively high temperature and a relatively high WHSV were applied, the selectivity is higher at a given conversion or, conversely, the conversion is higher at a given selectivity, as compared to the comparative experiments (Comparative Example 1) wherein a relatively low temperature and a relatively low WHSV were applied.

That which is claimed is:

1. A process for the oxidative dehydrogenation of an alkane containing 2 to 6 carbon atoms and/or the oxidation of an alkene containing 2 to 6 carbon atoms, wherein a gas stream comprising oxygen and the alkane and/or alkene is contacted with a mixed metal oxide catalyst containing molybdenum, vanadium, niobium and optionally tellurium, and wherein the weight hourly space velocity is from 2.1 to 25.0 $hr^{-1}$ and the temperature is of from 300 to 500° C.

2. The process according to claim 1, wherein the weight hourly space velocity is from 4.0 to 18.0 hr-1.

3. The process according to claim 1, wherein the temperature is from 310 to 450° C.

4. The process according to claim 1, wherein a pressure is from 0.1 to 15 bara.

5. The process according to claim 1, wherein the process is a process of the oxidative dehydrogenation of an alkane containing 2 to 6 carbon atoms and wherein said alkane is ethane or propane.

6. The process according to claim 1, wherein the process is a process of the oxidation of an alkene containing 2 to 6 carbon atoms and wherein said alkene is ethylene or propylene.

* * * * *